United States Patent [19]

Polomsky et al.

[11] Patent Number: 4,741,044
[45] Date of Patent: Apr. 26, 1988

[54] PROCESS FOR FAULT DETECTION ON DEFINED STRUCTURES

[75] Inventors: Horst Polomsky, Untergruppenbach; Rolf Jäger, Talheim, both of Fed. Rep. of Germany

[73] Assignee: Telefunken Electronic GmbH, Heilbronn, Fed. Rep. of Germany

[21] Appl. No.: 758,809

[22] Filed: Jul. 25, 1985

[30] Foreign Application Priority Data

Jul. 28, 1984 [DE] Fed. Rep. of Germany ....... 3427981

[51] Int. Cl.$^4$ ............................................. G06K 9/46
[52] U.S. Cl. ......................................... 382/8; 358/106; 358/101; 356/237
[58] Field of Search ............................. 382/8, 34, 101; 358/106; 356/237

[56] References Cited

U.S. PATENT DOCUMENTS

| | | |
|---|---|---|
| 4,148,065 | 4/1979 | Nakagawa et al. ................... 382/8 |
| 4,152,723 | 5/1979 | McMahon et al. .................. 358/106 |
| 4,223,387 | 9/1980 | Danielsson et al. ..................... 382/8 |
| 4,288,782 | 9/1981 | Bader et al. ............................ 382/34 |
| 4,403,294 | 9/1983 | Hamada et al. ..................... 358/106 |
| 4,442,542 | 4/1984 | Lin et al. ................................. 382/8 |
| 4,479,145 | 10/1984 | Azuma et al. ........................... 382/8 |
| 4,651,341 | 3/1987 | Nakashima et al. .................... 382/8 |

Primary Examiner—Leo H. Boudreau
Assistant Examiner—Steven Brim
Attorney, Agent, or Firm—Spencer & Frank

[57] ABSTRACT

The invention relates to a process for fault detection on structures on surfaces of electrical components or the auxiliary means required to manufacture these components, wherein the actual structure provided in each respective case is scanned with a test beam. In accordance with the invention, provision is made for structure faults or structure deviations to be directly ascertained from sequences of picture points within the scope of an ordinate scanning.

21 Claims, 6 Drawing Sheets

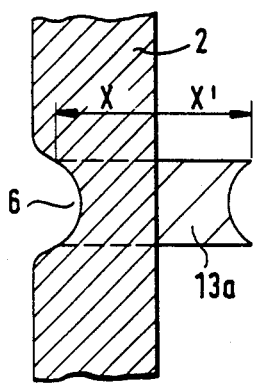
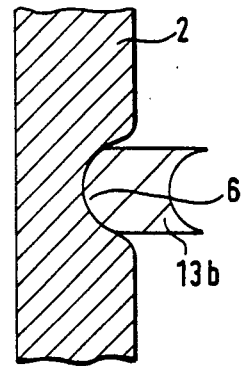
FIG. 4a  FIG. 4b
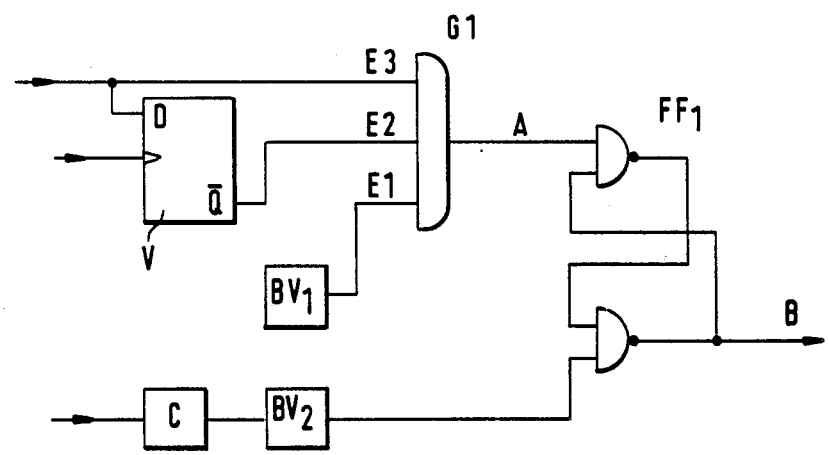
FIG. 4c

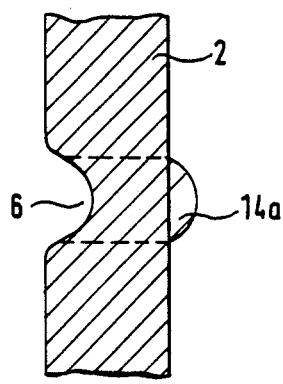
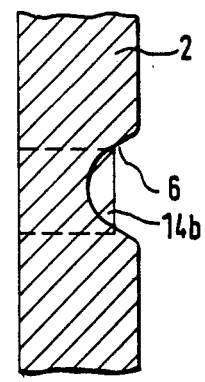
FIG. 5a   FIG. 5b
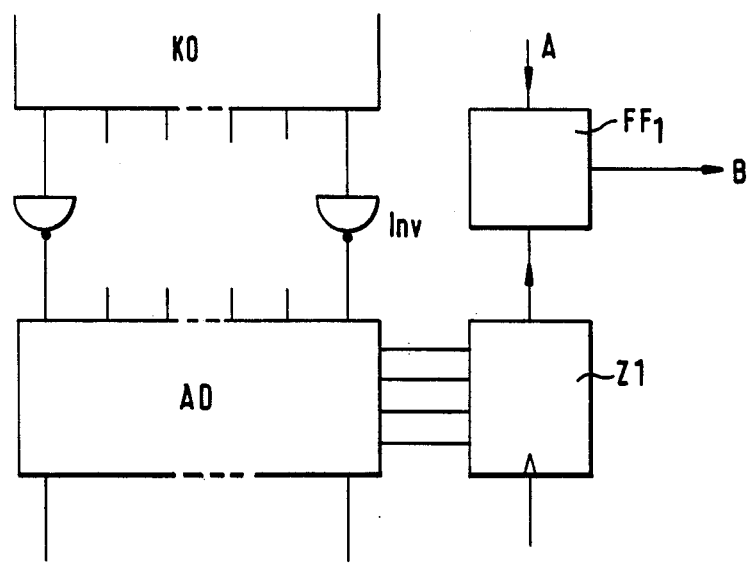
FIG. 5c

4,741,044

PROCESS FOR FAULT DETECTION ON DEFINED STRUCTURES

BACKGROUND OF THE INVENTION

The invention relates to a process for fault detection on defined structures on surfaces of electrical components or the auxiliary means required to manufacture these components, wherein the actual structure provided in each respective case is scanned with a test beam.

In the manufacture of semiconductor components, for example, both the required sets of masks and the single semiconductor discs and semiconductor components must be checked optically for faults in the desired structures during the manufacturing processes. Since in the course of technological development, the component structures become smaller and smaller and the integrated circuits grow more and more complex, also the necessary structure testing becomes increasingly difficult and technically more elaborate. In view of the great complexity and the resulting high development and manufacturing costs of integrated circuits, the detection of structure faults or structure deviations at as early a stage of the development and manufacture as possible is gaining more and more significance. Optical testing of the highly integrated circuits and the masks required for their manufacture under a microscope is no longer purposeful.

Several processes have meanwhile been suggested for testing and controlling structures on semiconductor discs or masks by machine. In one process, an actual structure is compared with a second actual structure by means of fragmented, optical ray paths. The two pictures may also be made to register in the form of a video picture, with the composition picture then being evaluated.

In another known process, the structure to be tested is scanned with the aid of a test beam and decomposed into picture points. The thus digitalized total picture is put into a data processor in which the scanned structure is compared to desired pictures, desired structures or structure regulations contained in a store. Such a process is, for example, described in German patent application No. P 27 00 252.4.

In the first above-decribed process, structure faults are detected from a non-registration of the two composite pictures, whereas in the second above-mentioned process, fault detection is only possible after a comprehensive data processing operation. Both known processes require enormous optical and electronic expenditure.

SUMMARY OF THE INVENTION

The object underlying the present invention is therefore to indicate a simple testing and controlling process for structures on electrical components, in particular, on semiconductor discs and semiconductor masks, wherein neither optical comparison of two actual structures nor scanning and computer processing of complete pictures of the structures to be tested is necessary. The inventive process should involve as little circuitry expenditure as possible and enable to least a large amount of the fault possibilities occurring to be permanently indicated during the scanning procedure.

This object is attained in a process of the kind mentioned at the outset in that structure faults or structure deviations are directly detected from sequences of picture points within the scope of an ordinate scanning.

The inventive process is based on the fact that structure faults have laws of their own and therefore only these laws need be tested to detect the structure faults. Such structure fault laws are essentially governed by shape, color and material of the fault.

The ordinate-type examination of structures indicated that in the case of a cross-coordinate measurement, over 80% of the defects discovered exhibited measurements which fell short of or exceeded the preset dimensions of the structures. The automatic checking in accordance with the invention therefore enables use of a measurement window with which, for example, a geometric structure below or above the given structure measurements is measured. With these measurement windows, only such structure elements as lie within the preset measurement window and do not coincide with the defined structure measurements are then detected.

In the inventive process, the structures may, for example, be scanned with a laser beam, an electron beam or a light beam, with the scanning being performed in transmitted light or incident light. The scanning signal is decomposed into the number of picture points required for the desired resolution. The above-described ordinate scanning is preferably carried out axially parallel to the edge surfaces of the components or the masks, with preferably a defined and limited number of successive picture points being detected in the on-line-processing, and electronic means being provided for subjecting at a structure transition or a structure edge the previously detected picture points to an evaluation from which any existing structure faults or structure deviations then become apparent. For coverage of a total structure, use may be made of different evaluating means or evaluating units whose association with the picture points detected in each respective case is synchronized with the scanning procedure. This enables variation of the aforementioned measurement windows in the course of the scanning procedure.

Further advantageous practical examples of the inventive process and of the electronics required for the evaluation are apparent from the subclaims.

BRIEF DESCRIPTION OF THE DRAWINGS

The invention will now be explained in greater detail with reference to embodiments.

FIGS. 4a and 4b show a conduction path structure with a faulty indentation and the type of fault registration.

FIG. 4c shows the electronics for the recognition of the fault according to FIGS. 4a and 4b.

FIGS. 5a and 5b similarly show conduction path structures with faulty indentations, but with a different type of fault illustration.

FIG. 5c shows the pertinent data acquisition for the fault recognition according to FIGS. 5a and 5b.

DESCRIPTION OF THE PREFERRED EMBODIMENTS

Figure 1:
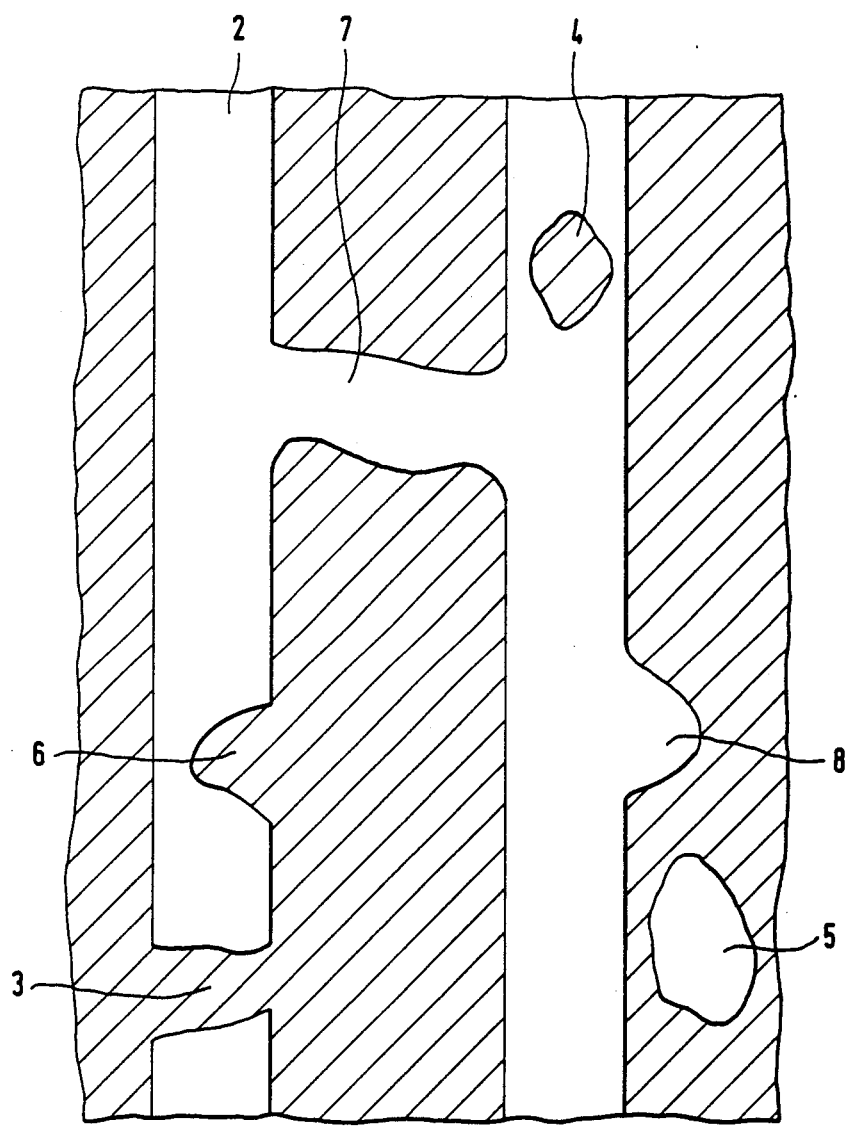
FIG. 1 shows a section of a structure with various possible structure faults.

FIG. 1 shows a section of a structure as it occurs, for example, in the conduction path plane of an integrated semiconductor circuit. This structure contains some typical structural defects. The structure is, for example, comprised of two parallel, lightly illustrated aluminum conduction paths 2 connected to one another by a conduction path bridge 7. The conduction path comprises constrictions 6 and bulges 8. There is also a conduction path interruption 3. At one point, the conduction path exhibits a hole 4; at another point, there is an undesired conduction path spot 5.

In the ordinate scanning of the structure for fault recognition, a measurement window corresponding, for example, to the desired width of the conduction path 2 is defined. This measurement window which during the structure scanning wanders, in the figurative sense, with the scanning procedure over the structure, has, for example, a width of 2–3 µm, with the conduction paths 2 being of corresponding width. In the on-line scanning, faults caused by a hole 4, a constriction 6, a conduction path interruption 3 or a conduction path left-over 5 are now perfectly detected.

Figure 2A:
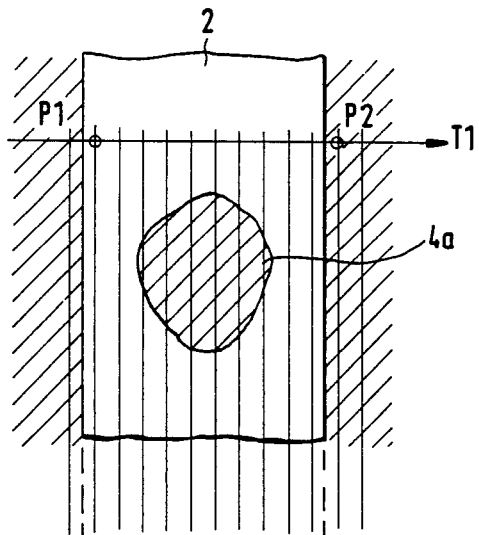
FIG. 2a shows a conduction path with an inclusion.

FIG. 2a shows a conduction path structure containing a faulty inclusion 4a. The conduction path structure is scanned along the ordinate lines with, for example, a laser beam, an electron beam of a light beam, and the scanned picture is decomposed into single picture points. In the case of scanning along the ordinate line T1 it is still a fault-free structure and there can therefore be no fault recognition in the evaluation. The number of picture points pixels detected via the aforementioned measurement window and subjected to an evaluation corresponds, for example, to the desired width or the desired length of the structures occurring, in the embodiment according to FIG. 2a, for example, to the width of the test path 2. This desired spacing corresponds in one embodiment to 10 picture points. During the scanning, the picture points are continuously entered into a register which evaluates only the number of picture points provided for the on-line-detection, i.e., in the embodiment 10 picture points. Also provided is a logic 11 according to FIG. 2b which detects a structure edge or the structure transition. At the structure transition, the contents of the register are compared with those of a comparison register by suitable electronic means, with the presence or absence of a structure fault resulting from the number of coincidences of the information contained in the register and in the comparison register.

Figure 2B:
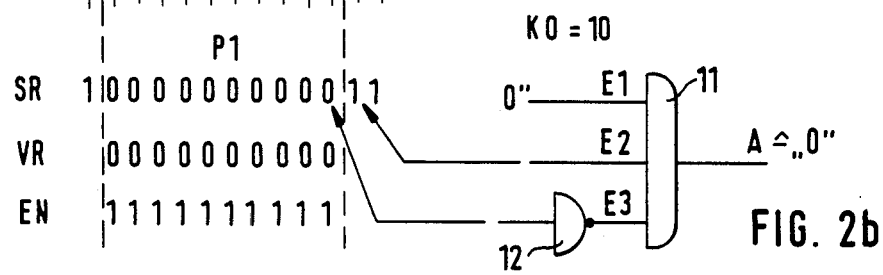
FIGS. 2b and 2c show the data acquisition in the ordinate scanning in a fault-free conduction path area.
Figure 2C:
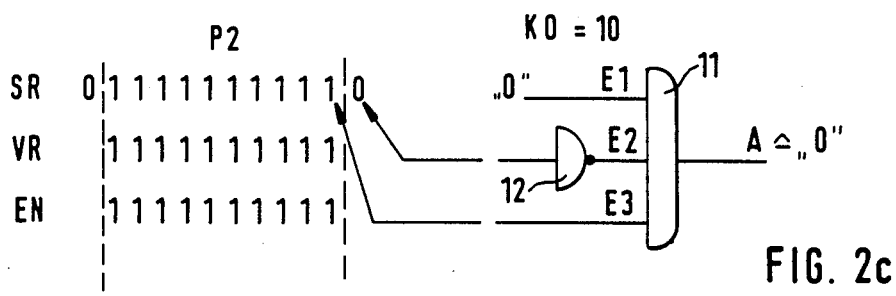

In accordance with FIGS. 2b and 2c, error checking may be carried out both at the transition from dark structure areas to light structure areas and at the transition from light structure areas to dark structure areas. A dark picture point is evaluated with a logical "0" and a white picture point with a logical "1". In the structure of FIG. 2a, there is a black/white transition at the point P1. Since in the case of a perfect structure, the 10 picture points preceding the point P1 were dark, the shift register SR contains 10 "0" information data in accordance with FIG. 2b. The subsequent first picture point in the light area which is fed into the input E2 of the AND gate 11, is, however, a "1". The comparison register VR similarly contains 10 "0" picture points in accordance with the definition of the measurement window. In a correlator, the contents of the shift register SR are now compared with the contents of the comparison register VR, with the comparison in all 10 picture points being enabled, in the embodiment, by the unit EN. The correlator may comprise means by which certain picture points in the register are not taken into consideration in the evaluation. In this case, gate circuits in the correlator which effect the comparison between individual picture points in the register and in the comparison register may be externally forcibly set by the unit EN (enable). Picture points read out via forcibly set gates are therefore not taken into consideration in the evaluation.

In the scanning at the point P1 in accordance with FIG. 2b, the last picture point in the shift register SR is fed via an inverter 12 to the input E3 of the AND gate 11. In accordance therewith, the newly arriving picture point corresponding to a "1" reaches the input E2 of the AND gate 11. The signal corresponding to the correlator evaluation is fed to the input E1 of the AND gate. In the event of coincidence in 10 picture points, there appears at the correlator output a "0" so that the output signal A of the AND gate is also a "0", which corresponds to the definition of a fault-free structure.

A corresponding testing may be carried out at the transition from the light structure area to the dark structure area at the point P2 of the ordinate scanning T1. In accordance with FIG. 2c, white picture points are again defined as "1" and black picture points as "0". At the point P2, the shift register SR consequently contains only 10 picture points with the logical value "1", since the spacing between the points P1 and P2 corresponds exactly to 10 picture points and no dark structure areas occur in this area. The comparison register also contains only logical "1" values in the white/black testing. In the embodiment, the enable unit EN in the correlator ensures that all 10 picture points in the shift register SR and in the comparison register VR are compared with one another. At the AND gate 11, the last picture point in the shift register is fed to the input E3. The first picture point in the dark area to arrive is inverted and also reaches the AND gate 11 via the input E2. The correlator again ascertains a coincidence in 10 picture points, so that a "0" reaches the input E1, and the output signal A of the AND gate 11 is "0", which corresponds to a fault-free structure.

Figure 2D:
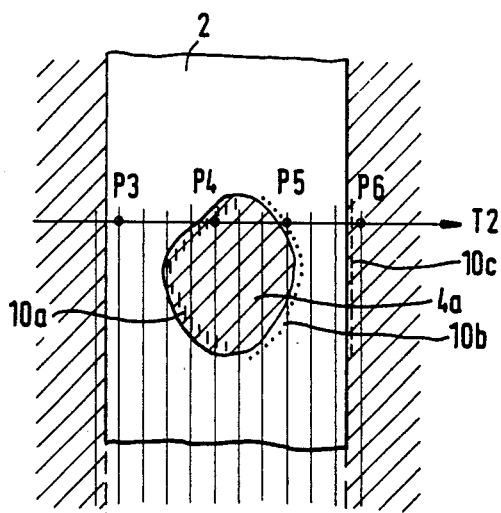
FIG. 2d again shows the structure according to FIG. 2a in an ordinate scanning in the faulty area.
Figure 2E:
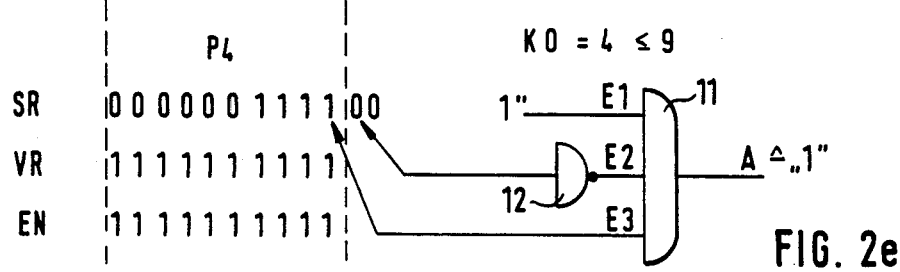
FIGS. 2e, 2f and 2g show the data acquisition and registration of the structure fault.
Figure 2F:
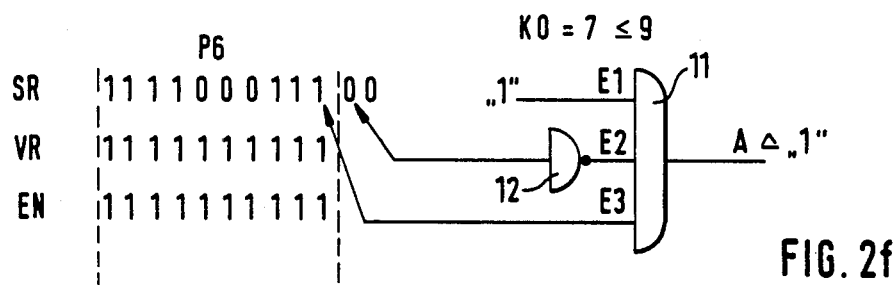

FIG. 2d again shows the structure of FIG. 2a; however, now the ordinate scanning is carried out in the area of the line T2 and thus in an area in which a faulty location 4a occurs. The black/white transition at the point P3 corresponds to the transition at the point P1 (FIG. 2a) so that there is no fault reporting at the point P3. At the point P4, the scanning beam enters the dark area of the faulty structure 5a. In accordance with FIG. 2e, a logical "1" is therefore followed by a logical "0", so that both inputs E2 and E3 of the AND gate 11 are set at "1". The shift register SR contains at this point in time only 4 "1" values corresponding to the spacing between the points P3 and P4. All other storage places in the shift register SR are, on the other hand, set at "0", with these "0" values still originating from the dark area outside of the conduction path 2. In a white/black testing, however, all storage places in the comparison register VR are set at "1". Accordingly; in the comparison in the correlator only a coincidence in 4 picture points is ascertained. The correlator is so designed that in the event of a coincidence in 9 or less picture points, a logical "1" is emitted. In this case, the input E1 of the AND gate 11 therefore also acquires a "1", so that the output A is also set at "1", which corresponds to a faulty structure.

A white point on a black background, which corresponds to a faulty location, then appears on the screen. In the total picture scanning, a white line 10a corresponding to the left envelope curve line of the faulty structure 4a therefore appears on the screen.

A further white/black transition occurs at the point P6. In this case, the shift register contains, departing from the point P6, 3 "1" values corresponding to the spacing between P6 and P5, 3 "0" values corresponding to the spacing between the points P4 and P5, and 4 "1" values corresponding to the spacing between the points P4 and P3. Accordingly, in the correlator a coincidence with only 7 picture points is ascertained, which again results in a correlator output signal "1", so that the output signal A at the AND gate 11 is set at "1", which corresponds to a fault. In the total scanning, therefore occurs a light line 10c on a dark background in the screen reproduction.

Figure 2G:
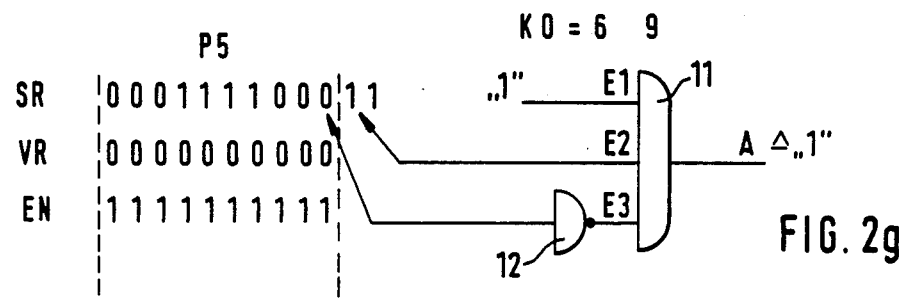

At the point P5, there was a black/white transition whose data acquisition is reproduced in FIG. 2g. At the point P5, the shift register contents, departing from the point P5, are 3 times "0" corresponding to the width of the faulty structure, 4 times "1" corresponding to the spacing between the points P4 and P3, and 3 times "0" corresponding to dark picture points left of the conduction path 2. The inputs E2 and E3 of the AND gate 3 are set at the transition point P5 at "1". The correlator ascertains a coincidence in 6 picture points, so that also the input E1 and thus the output A are set at "1", which again indicates a fault. In the black/white scanning of the total structure, there therefore occurs the line 10b corresponding to the right envelope curve half of the faulty structure 4a.

Figure 2H:
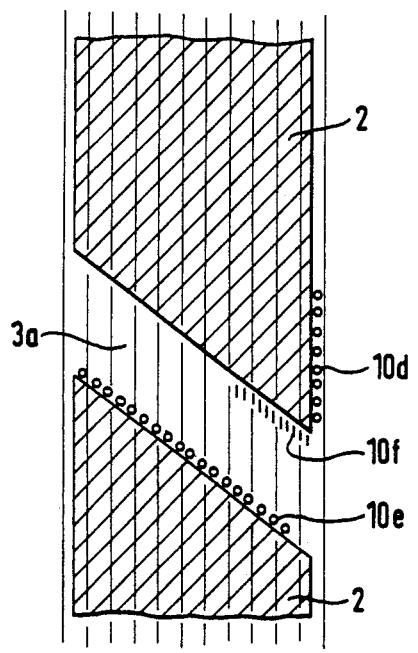
FIGS. 2h and 2i show conduction path interruptions and the type of recognition of the fault.

FIG. 2h shows a conduction path interruption of a dark conduction path which is so designed that at a white/black transition, at least in one certain area, both conduction path sections are detected. The line 10f therefore indicates a faulty structure in the white/black testing. The lines 10d and 10e, on the other hand, occur in the testing of the black/white transitions since in these areas the shift register SR contains insufficient picture points corresponding to black.

Figure 2I:
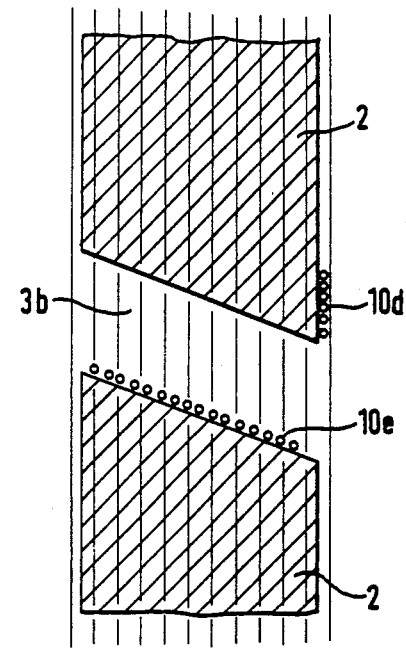

In the structure according to FIG. 2i, there is a conduction path interruption, however, the conduction path ends are spaced so far apart that a faulty white/black transition is no longer registered in the ordinate scanning. The fault is nevertheless recognized since it is ascertained in the testing of black/white transitions and registered with the lines 10d and 10e that the shift register does not contain sufficient picture points corresponding to black over a certain area of the ordinate scanning. The conduction path interruptions are designated in FIGS. 2h and 2i by 3a and 3b, respectively.

Figure 3:
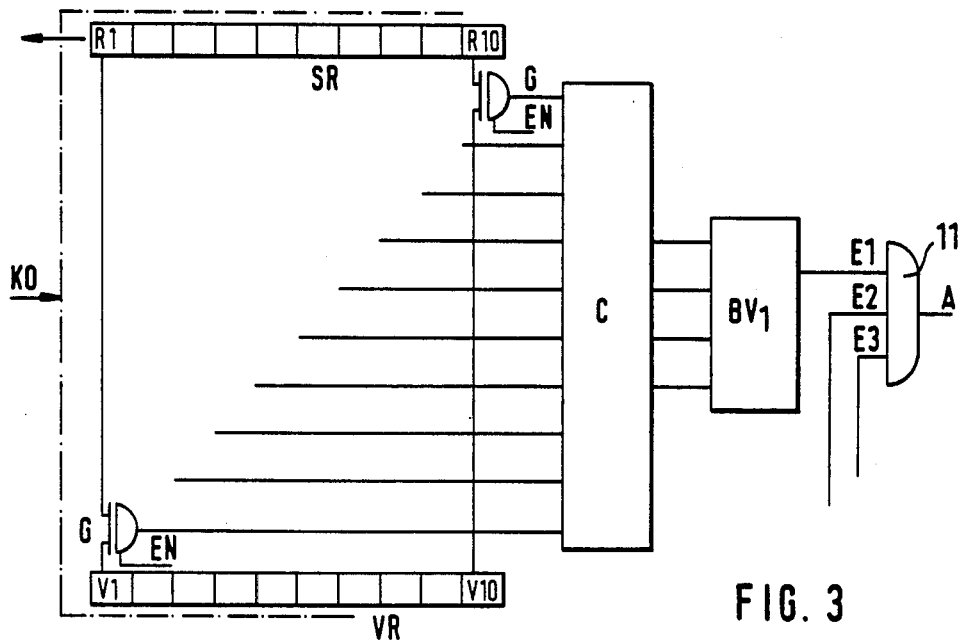
FIG. 3 shows an embodiment for the design of the data acquisition system, with which structure faults are recognized via a logic.

FIG. 3 shows a correlator KO as may be used for evaluation and registration of faulty structures. The correlation contains a shift register SR which may accommodate, for example, the picture points R1 to R10 in digital form. The comparison register VR contains at corresponding storage places digital information V1–V10, corresponding to the desired picture of a structure. The contents of this comparison register are preset. It is now ascertained via logic gate circuits G whether the register contents of associated cells in the shift register SR and in the comparison register VR coincide.

In the embodiment, the comparison is effected, for example, with the aid of 10 exclusive OR gates G. Via the control input EN, the gates may be forcibly set to coincidence if certain picture points within the measurement window comprising 10 bits are not to be taken into consideration in the evaluation. A coder C summarizes the output signals of the gate circuits G and converts the number of coincidences into a binary number which is fed, for example, to a binary comparator $BV_1$ containing a certain preset comparison number. The output of the binary comparator $BV_1$ is fed to the input E1 of the AND gate 11. The binary comparator may, for example, contain as preset comparison number the Figure 9, which means that if 9 or less cell contents coincide in the correlator, a logical "1" is issued at the binary comparator $BV_1$. If, on the other hand, there are 10 coincidences, a logical "0" appears at the input E1 of the AND gate 11. The extent of coincidence may be freely selected by the presetting of the comparison number.

In a further development of the invention, there is generated, upon registration of a structure fault at a structure edge or a structure transition, a secondary signal B which is terminated in the case of progressive structure scanning only after the number of coincidences in the correlator falls short of a preset value. This process wherein the faulty structures are reproduced more clearly, shall be explained with reference to FIGS. 4a to 4c. FIG. 4a shows a conduction path 2 comprising an indentation 6 at the left edge. FIG. 4b comprises a faulty indentation 6 at the right edge of the condution path 2.

In accordance with FIG. 4c, the picture points arrive successively at the input E3 of the AND gate G1, with the digitalized picture being simultaneously fed to the delay and reverse member V. The inverted output of this delay member V, consisting, for example, of a flip-flop, is fed to the input E2 of the AND gate 11. The delay constitutes one picture point, so that at a black/white transition a logical "1" occurs at both the input E2 and the input E3 of the AND gate 11. The binary comparator $BV_1$ feeds the signal gained from the correlator evaluation to the input E1 of the AND gate. In an ordinate scanning in accordance with FIG. 4a, a fault signal will therefore occur at the output A of the AND gate when the scanning beam travels over the area of the indentation. A flip-flop $FF_1$ which produces a secondary signal B is set by the output signal A which corresponds to a "1" in the selected definitions. This flip-flop $FF_1$ is only reset again to terminate the signal B at a drop below a defined number of coincidences in the correlator. The number of coincidences can again be obtained from the coder C whose binary number is fed to a second binary comparator $BV_2$ which causes the flip-flop $FF_1$ to be reset when there is a drop below the preset comparison number in the binary comparator $BV_2$. A resetting of the store flip-flop $FF_1$ may, for example, occur when the shift register SR no longer contains a picture point "0" corresponding to black. The output signal B then records the line X' in accordance with FIG. 4a, which corresponds to the width X of the conduction path structure. In this way, the fault is stored and reproduced as mirrored structure 13a in accordance with FIG. 4a.

In the same way, the fault in the structure according to FIG. 4b is reproduced, so that it can be read off from the left edge line of the structure 13a and 13b, respectively, whether there is an indentation at the left or the right edge of the conduction path structure. In the case of an indentation at the left edge of the conduction path structure, a straight left edge surface of the structure 13a indicating the fault is obtained, whereas in the case of an indentation at the right edge of the conduction path structure, the left edge of the indication structure 13b corresponds to the course of the indentation.

In order to indicate the extent of a faulty structure at the occurrence of a structure edge or a structure transition, it is also possible, in an advantageous further development of the invention, to subtract the number of coincidences in the correlator from the desired value of the coincidences. The resulting binary number is fed to a counter Z1 which is preset by this number. The counter triggers a secondary signal which does not terminate until the counter with the picture point frequency has counted down from the preset number to the value "0" or another preset value. This shall be explained with reference to FIGS. 5a to 5c.

FIG. 5a again shows a conduction path structure with an indentation 6 at the left edge, whereas in FIG. 5b a conduction path 2 with an indentation 6 at the right edge is illustrated. In accordance with FIG. 5c, an adder AD is now used and is fed from the correlator KO the inverted number of coincidences between shift register contents and comparison register contents. The inverter stages Inv serve to invert the correlator output signals. On the other hand, the adder is fed the required minimum width for the conduction path 2, i.e., for example, 9 times the digital "0", which corresponds to the desired width of a dark conduction path 2. In the adder AD, the actual number of coincidences is therefore subtracted from the desired number of coincidences.

The result of this calculating procedure is fed as binary number to the counter Z1 which is preset by this binary number and is now counted down with the clock frequency of the picture point scanning to the value "0". When the counter Z1 is preset, a secondary signal B occurs at the output of the counter Z1 by which the flip-flop $FF_1$ is set. The flip-flop $FF_1$ is reset when the counter Z1 has counted down, for example, to the value "0". The output signal at the flip-flop $FF_1$ therefore indicates the faulty structure 14a and 14b in accordance with FIGS. 5a and 5b, respectively. For example, in the center of the indentation 6 in FIG. 5a, the difference between the desired value of coincidences and the actual coincidences in the correlator constitutes the value of 3 picture points. In this case, the counter Z1 is set at 3 and is set back again to the value "0" during the countdown. In this way, a broad line equivalent to 3 picture points which corresponds to the crest line of the structure 14a is produced. Thus, a true reproduction of the faulty structures is obtained by the illustration of the areas 14a and 14b.

The inventive process may be extended by the structures also being scanned vertically in a further test run or paralle, and by picture point sequences of defined length being evaluated in each case during the on-line-processing in the vertical direction. Here, faults are recognized which, for example, remain undiscovered by the horizontal ordinate detection, which results in an increase in the fault detection quota.

Structure edges or structure transitions may also be defined by color changes or by material changes in the scanned picture. In the case of color changes, video systems enabling color decomposition of the scanned signal may be used for the scanning. On the other hand, selective recognition processes permitting recognition of material differences or color differences may also be used. Color filters or for the recognition of different materials, the use of fluorescence aids are, for example, suitable. With the fluorescence, the photoresist arranged on the surface of a semiconductor disc is, for example, excited with light until it emits photons. A camera only photographs the emitted band spectra, so that the photoresist which may possibly not differ with regard to color from the rest of the semiconductor surface becomes visible. In this way, material differences or also only slight color differences may in each case be converted into genuine light/dark transitions. The electronic recognition means are then so designed that the evaluation of the register contents may be effected at both the transition from the light into the dark area and from the dark into the light area. The process only produces white surfaces on a black background if faults are present.

Rapid fault finding may at first only be limited to reacting to white picture points (log "1") which appear, and then, if required, to introducing a further examination (e.g. as to shape or surface size), which may be more time consuming. The fault pictures acquired, containing only the structure faults or structure deviations detected with the inventive process, may be reproduced directly via a screen, or they may be stored in an advantageous way in the form of reproducible pictures. The fault pictures may, for example, be recorded onto video tapes.

What is claimed is:

1. Process for fault detection on defined structures on surfaces of electrical components or the auxiliary means required to manufacture these components, comprising scanning the actual structure with a test beam which traces a succession of scanning lines to produce successive picture elements associated with each scanning line, and directly determining structural faults or structural deviations from the sequences of picture elements, wherein said step of directly determining comprises: continuously writing representations of successive picture elements into a shift register capable of storing only a selected number of picture elements; providing fixed representations of a number of successive picture elements in a comparison register; logically processing selected representations in the shift register for detecting structural edges or structural transitions present in the actual structure; comparing, upon each such detection, the contents of the shift register and the comparison register contents to determine the number of coincidences between those; indicating the presence or absence of a structural fault or structural deviation as a function of the number of coincidences between the representations contained in the shift register and comparison register; and storing only representations of indicated structural faults or structural deviations in the form of data or of reproducible images.

2. Process according to claim 1, wherein the structures are scanned with a laser beam, electron beam or light beam, to produce a scanning signal which is decomposed into the picture elements.

3. Process according to claim 1, wherein the scanning is carried out in transmitted light or incident light.

4. Process according to claim 2, wherein said step of scanning is carried out with a video system for producing a scanning signal which is subjected to color decomposition for selective recognition of materials and/or colors.

5. Process according to claim 4, wherein fluorescence effects or color filters are used for selective recognition processes.

6. Process according to claim 1, wherein the structures are scanned axially parallel to the edge surfaces of the components or the auxiliary means.

7. Process according to claim 1, wherein a defined and limited number of successive picture elements is detected during said step of determining, and wherein means are provided to subject at a structure transition or a structure edge the previously detected picture element representation to an evaluation from which any existing structure faults or structure deviations become apparent.

8. Process according to claim 7, wherein different evaluating means or evaluating units whose association with the picture elements detected in each respective case is synchronized with the scanning procedure, are provided for a structure scanning.

9. Process according to claim 7, wherein the number of picture elements detected and subjected to an evaluation corresponds to the desired width or desired length of a structure.

10. Process according to claim 1, wherein the shift register contents are compared in a correlator with the comparison register contents, and said step of indicating includes comparing the number of coincidences with a preset comparison number, and in the event that the latter is not reached, a signal is provided such that at the structure edge of the structure transition, a structure fault indication is produced.

11. Process according to claim 10, wherein the number of coincidences in the correlator is converted in acoder (C) into a binary number which is fed to a binary comparator ($BV_1$) containing the preset comparison number.

12. Process according to claim 1, wherein upon registration of a structure fault at a structure edge or a structure transition, a secondary signal (B) is generated and, in the case of progressive structure scanning, is not terminated until the number of coincidences falls short of a preset value.

13. Process according to claim 12, wherein the secondary signal (B) is generated by setting a flip-flop ($FF_1$) which is set back again to terminate the signal when there is a drop below the preset number of coincidences.

14. Process according to claim 12, wherein the secondary signal (B) is terminated when the number of coincidences between shift register and comparison register contents is zero.

15. Process according to claim 8, wherein to indicate the extent of a missing structure upon occurrence of a structure edge or a structure transition, the number of coincidences is subtracted from a desired value of the number of coincidences, and wherein a counter (Z1) is preset with the resulting binary number and triggers a secondary signal (B) which terminates when the counter (Z1) with the picture element frequency has counted down from the preset number to the value zero.

16. Process according to claim 15, wherein upon appearance of the preset number, the counter (Z1) sets a flip-flop ($FF_1$) which is set back by the counter when the value zero is reached.

17. Process according to claim 15, wherein an adder (AD) to which the correlator output signals are fed in inverted form, is used for subtracting the number of coincidences from the desired value of the number of coincidences.

18. Process according to claim 8, wherein the structures are scanned horizontally and vertically and evaluations of picture element sequences of defined length are carried out in each respective case.

19. Process according to claim 8, wherein structure edges or structure transitions are defined by color changes of the scanned picture elements, and wherein means are provided to carry out evaluations of the shift register contents in the event of color transitions of both possible kinds.

20. Process according to claim 1, wherein means (EN) are provided by which certain picture elements in the shift register are not taken into consideration in said indicating step.

21. Process according to claim 20, wherein said step of comparing is carried out in a correlator having gate circuits which effect the comparison between register contents and which may be externally forcibly set, so that picture elements which are read out via forcibly set gates are not taken into consideration in said comparing step.

* * * * *